United States Patent [19]

Tovey et al.

[11] Patent Number: 5,379,754

[45] Date of Patent: Jan. 10, 1995

[54] METHOD USING APPROXIMATING APPARATUS FOR HERNIA REPAIR

[75] Inventors: H. Jonathan Tovey, Milford; Douglas J. Cuny, Bethel, both of Conn.; Michael Ciccolella, Lake Carmel, N.Y.

[73] Assignee: United States Surgical Corporation, Norwalk, Conn.

[21] Appl. No.: 922,259

[22] Filed: Jul. 30, 1992

[51] Int. Cl.⁶ .................................................. A61B 1/00
[52] U.S. Cl. ......................................... 128/4; 128/898; 606/1; 606/151; 33/512; 33/490; 33/465
[58] Field of Search ................. 33/511, 512, 465, 484, 33/485, 490, 496, 495, 415, 418, 422, 452, 456, 467, 483, 514, 514.2, 513; 606/102, 96, 1, 213, 151; 623/11, 12; 128/4, 898

[56] References Cited

U.S. PATENT DOCUMENTS

| | | | |
|---|---|---|---|
| 728,137 | 5/1903 | Severance | 33/495 |
| 2,449,265 | 9/1948 | Williams | 33/483 X |
| 2,606,371 | 8/1952 | Klimek | 33/490 |
| 3,096,586 | 7/1963 | Albright et al. | 33/465 X |
| 3,740,779 | 6/1973 | Rubricuis | 33/512 X |
| 3,870,048 | 3/1975 | Yoon | 128/4 X |
| 3,938,504 | 2/1976 | Dickinson, III et al. | |
| 4,016,867 | 4/1977 | King et al. | |
| 4,223,445 | 9/1980 | Goodland | |
| 4,226,025 | 10/1980 | Wheeler | |
| 4,317,289 | 3/1982 | Conn | |
| 4,328,619 | 5/1982 | Lefevre et al. | |
| 4,358,898 | 11/1982 | Johnson | |
| 4,362,167 | 12/1982 | Nicolai et al. | |
| 4,394,801 | 7/1983 | Thibodeaux | |
| 4,489,732 | 12/1984 | Hasson | |
| 4,562,649 | 1/1986 | Ciavarella | |
| 4,685,474 | 8/1987 | Kurz et al. | |
| 4,721,098 | 1/1988 | Watanabe | |
| 4,726,121 | 2/1988 | Ray et al. | |
| 4,779,349 | 10/1988 | Odensten et al. | |
| 4,916,822 | 4/1990 | Johnson | |
| 5,010,892 | 4/1991 | Colvin et al. | |
| 5,013,318 | 5/1991 | Spranza, III | |
| 5,020,233 | 6/1991 | Syken | |
| 5,109,869 | 5/1992 | Buckley | |
| 5,116,357 | 5/1992 | Eberbach | 606/1 X |
| 5,122,155 | 6/1992 | Eberbach | 606/1 X |
| 5,176,692 | 1/1993 | Wilk et al. | 606/151 |
| 5,183,033 | 2/1993 | Wilk | 128/20 |
| 5,199,179 | 4/1993 | Baker | 33/456 X |

OTHER PUBLICATIONS

Hospital for Joint Diseases and the New York City Hospital, "A Simple Fixation Guide for Fractured Hips", Sloane, pp. 354–355.

Primary Examiner—Stephen R. Crow
Assistant Examiner—Karen A. Jalbert

[57] ABSTRACT

A method for using an endoscopic apparatus for measuring the size of a hernia defect comprising a handle which is pivotally attached to a measuring rod. The hernia defect is measured by a plurality of calibrations positioned along the measuring rod. The measuring rod includes a blunt tip at its distal end and further is adaptable for 180′ positioning relative to the handle.

4 Claims, 6 Drawing Sheets

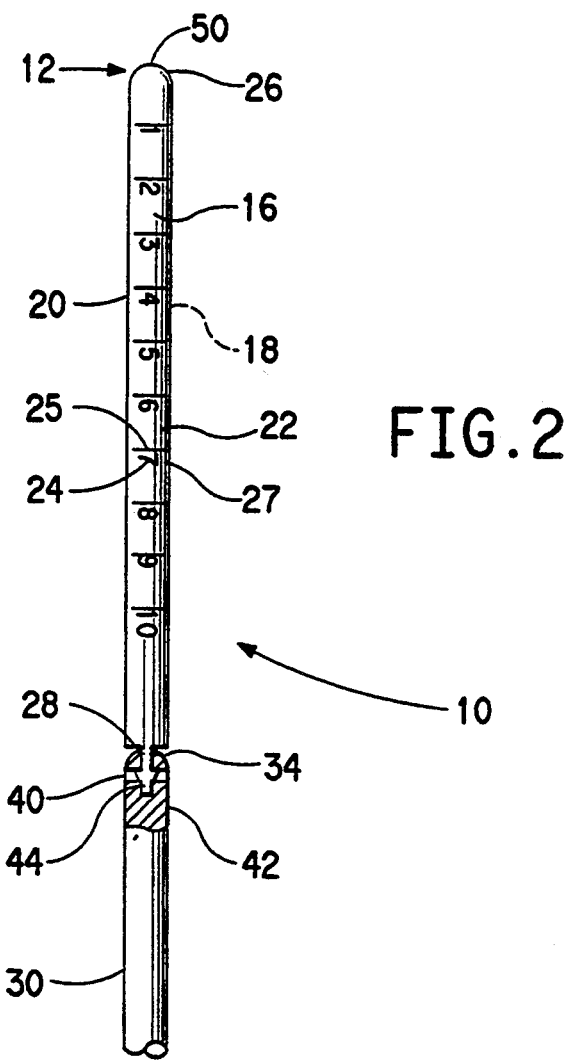
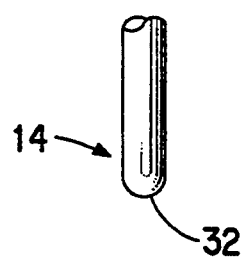
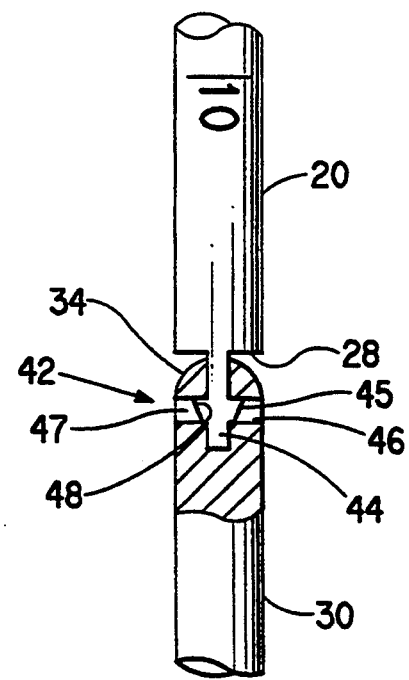

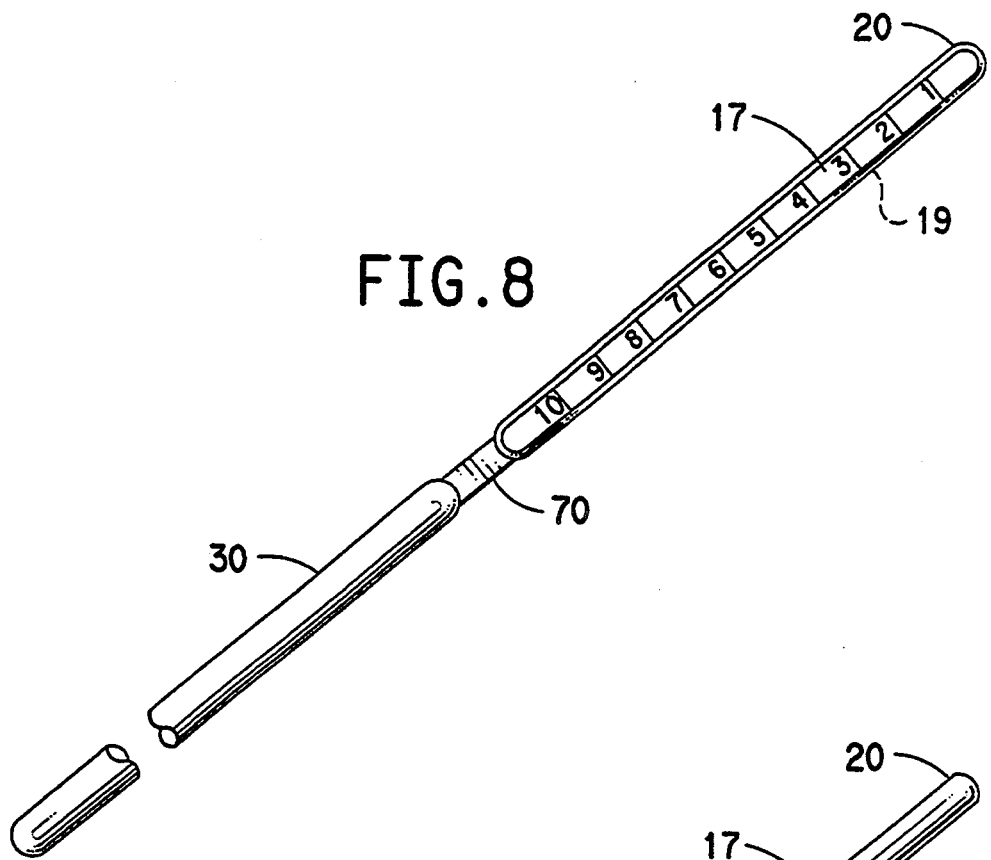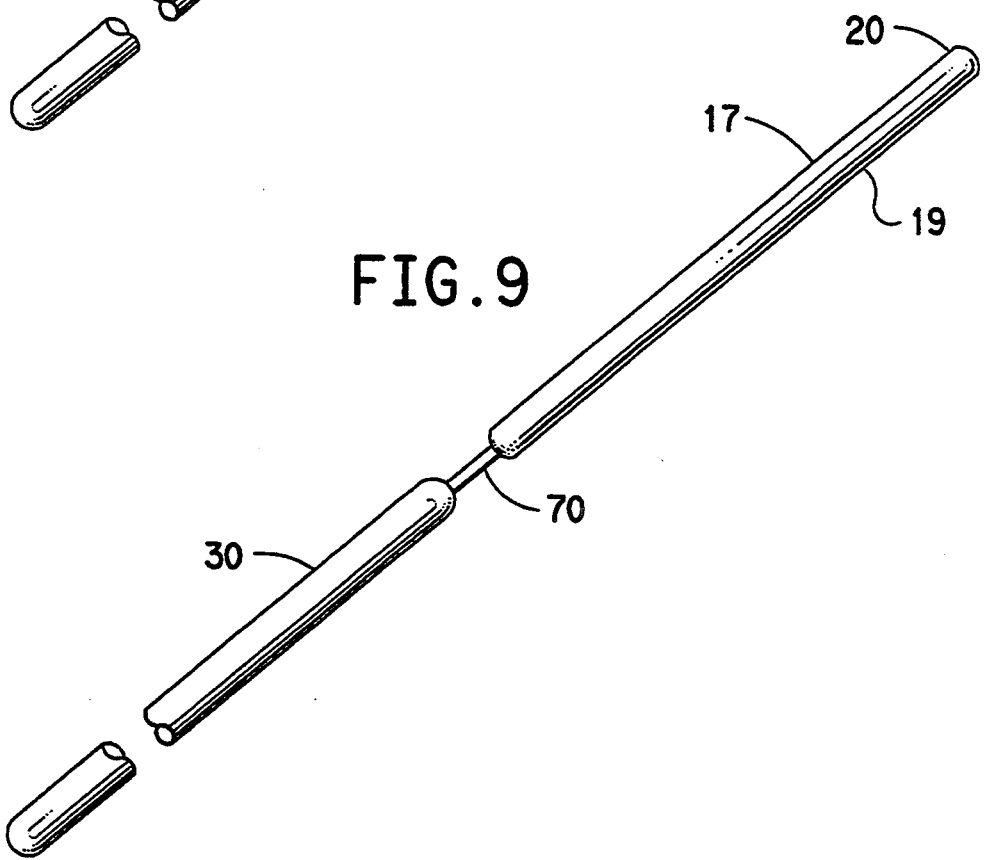

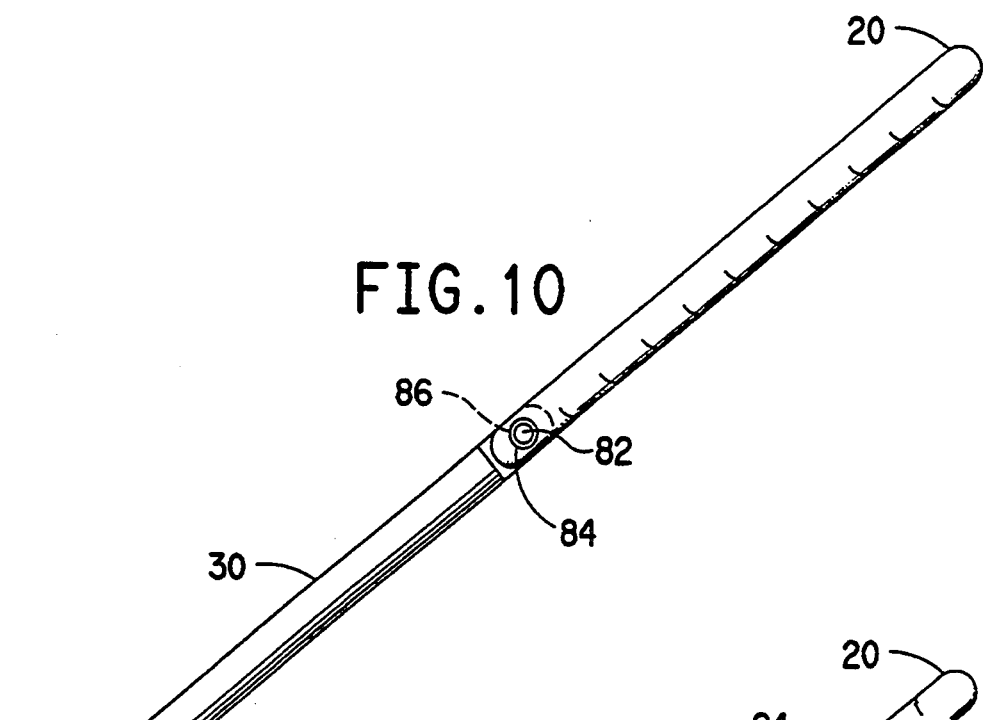
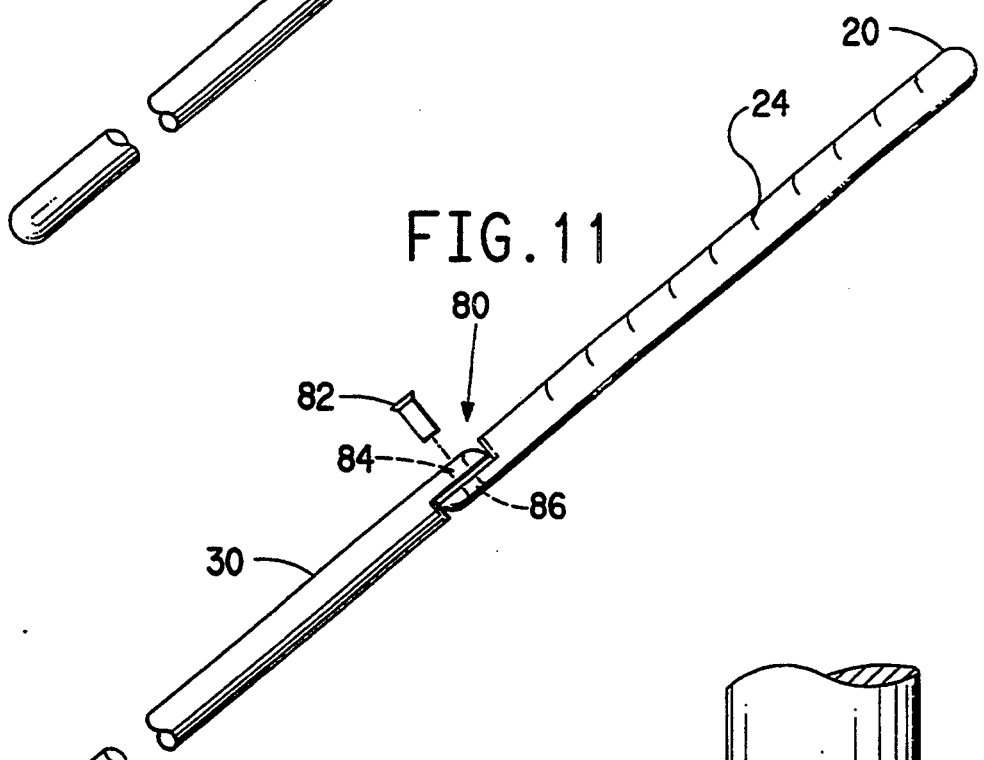
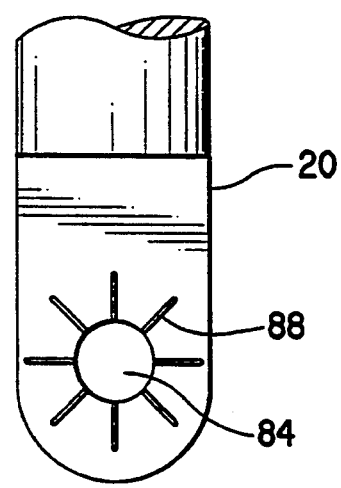

METHOD USING APPROXIMATING APPARATUS FOR HERNIA REPAIR

BACKGROUND OF THE INVENTION

1. Field of the Invention

The present invention relates generally to a measuring apparatus for surgical instrumentation and more particularly to an apparatus which effects measurement of a hernia defect to ascertain the corresponding necessary size of the repair material.

2. Background of the Invention

Hernias may be divided into three general classes—direct hernia, indirect hernia and femoral hernia. Direct or indirect hernias are usually characterized by a part of the intestine protruding through a defect n the supporting abdominal wall to form a hernia sac. This sac requires surgical repair which traditionally involved invasive repair and include a large incision. In order to reach the herniated portions, several layers of the abdominal wall must be separated. During the hernia repair procedure, to hernia is closed outside the abdominal wall in a manner which resembles the tying of a sack at the neck. A surgical mesh is usually then attached by sutures directly over the weakened abdominal wall opening to provide a reinforcement to the opening.

The above described traditional hernia repair amounts to a major invasive surgical procedure which frequently causes excessive trauma to the patient and results in an extended post-operative recuperative period. The need for cutting through the numerous tissue layers in order to access the herniated area also frequently causes severe trauma to the patient. Further, numerous complications related directly or indirectly to the surgery and including bleeding, infection, testicular atrophy, organ damage, nerve damage, blood vessel damage, etc., often enough result from repair performed by the traditional approach.

Today endoscopic surgery has replaced traditional hernia repair as the preferred procedure for correcting a wide variety of hernia defects. The benefits of endoscopic surgery for hernia repair include minimizing postoperative discomfort because no groin incision is made, minimizing the risk of injuries to the structures within the spermatic cord because the inguinal canal is not opened, and a reduction of migration because of the increased intraabdominal pressure holding the prosthetic mesh to the fascia. Endoscopic surgery also results in fewer of the above described complications.

In endoscopic procedures, surgery is performed in any hollow viscus of the body through narrow endoscopic tubes inserted through small entrance wounds in the skin; in laproscopic procedures, surgery is performed in the interior of the abdomen through a small incision. Laproscopic and endoscopic procedures generally require that any instrumentation inserted into the body be sealed, i.e., provisions must be made to ensure that gases do not enter or exit the body through the laproscopic or endoscopic incision as, for example, in surgical procedures in which the surgical region is insufflated. Moreover, laproscopic and endoscopic procedures often require the surgeon to act on organs, tissues and vessels far removed from the incision, thereby requiring that any instruments which are used in such procedures be long and narrow while being functionally controllable from one end of the instrument, i.e. the proximal end.

Endoscopic hernia repair is a minimally invasive procedure and is achieved by making several, usually three, small incisions in the abdomen through which a corresponding number of trocars are inserted. The various endoscopic instruments necessary to repair the hernia are inserted through the cannulas of these trocars. The endoscopic instruments inserted include a laparoscope for viewing the abdominal area, an apparatus for applying surgical staples to attach a prosthesis over the hernia opening, a prosthetic introducer and miscellaneous instruments such as graspers, dissectors and shears.

In an endoscopic procedure, the surgeon repairs the hernia by closing the hernia sac with a staple or clip and attaching a prosthesis over the opening similar to traditional hernia repair. In the endoscopic procedure, the proximal end of the various instruments which are located distally in the patient are manipulated and viewed by the surgeon through the laparoscope.

An essential part of the abdominal inguinal hernia repair procedure is the mesh prosthesis which closes either the internal inguinal or femoral ring and also reinforces the posterior wall of the inguinal canal. One example of a prosthetic material is polypropylene mesh sold under United States Surgical Corporation's trademark SURGIPRO. Alternatively, a piece of polytetrafluoroethylene (PTFE) can be rolled through a trocar and placed directly over the internal inguinal ring to cover the deep ring and posterior canal wall. Both of these prostheses are fixed in place by a surgical stapler.

The prosthesis to be applied should advantageously be tailored, i.e. sized, to correspond to the size of the defect to be repaired. Improper estimation of the size of the prosthesis requires withdrawal of the prosthesis through a trocar, resizing and repositioning in the preperitoneal location. Further, improper approximation can result in the waste of costly prosthetic material, a consideration not to be minimized in the current cost conscious health care environment. Also improper sizing requires that the patient remain under anesthia for a longer period of time, a negative even without the concern that hospitals bill based on the amount of time a patient actually spends in the operating room.

During a traditional hernia repair procedure, the surgeon could view the size of the defect and easily visually measure the size before preparing a correspondingly sized prosthetic. In endoscopic procedures, however, the herniated opening is far removed from the surgeon thereby preventing use of traditional and simple measurement techniques.

Presently during endoscopic hernia repair, the only way to approximate the size of the hernia defect is to view the image captured by the laparoscope and estimate the correct mesh size. Unfortunately, such estimates can be inaccurate and can result in the surgeon having to go through the aforementioned steps for withdrawal and resizing of the prosthesis.

Thus, there is a need to provide a device for accurately measuring the size of a hernia during an endoscopic repair procedure.

It would also be advantageous to provide a measuring device which is relatively inexpensive to manufacture.

SUMMARY OF THE INVENTION

A medical apparatus is provided for measuring the size of a body defect during an endoscopic procedure. The apparatus is not only intended for use in endoscopic hernia repair, and more particularly abdominal inguinal hernia repair, but is capable of being used in a wide variety of surgical laproscopic procedures.

The apparatus comprises an elongated handle and a measuring rod which is pivotally attached to the handle by a hinge. This pivotal attachment permits positioning and 180′ rotation of the measuring rod with respect to the handle. The measuring rod has calibrations printed along its top and bottom sides for measurement of the abdominal hernia. The distal end of the handle is manipulated by the surgeon to position the measuring rod with respect to the hernia opening to measure the size of opening. With this measurement of the hernia, the surgeon can properly tailor the size of the prosthesis material which will be used to close and reinforce the abdominal wall.

BRIEF DESCRIPTION OF THE DRAWINGS

For a further understanding of the objects of the present invention, reference is made to the following detailed description of preferred embodiment which is to be taken in connection with the accompanying drawings, wherein:

FIG. 2 is a side view of an apparatus in accordance with the present invention in a non-articulated position;

FIG. 3 is an exploded perspective view of an attachment mechanism of the apparatus shown in FIG. 2;

FIG. 8 is a top view of an apparatus in accordance with the present invention;

FIG. 9 is a side view of the apparatus shown in FIG. 8;

FIG. 10 is a top view of an alternative apparatus in accordance with the present invention; and FIG. 11 is a side view of the apparatus shown in FIG. 10; and FIG. 12 is an enlarged top view of an attachment mechanism of the apparatus shown in FIG. 10.

DETAILED DESCRIPTION OF THE PREFERRED EMBODIMENTS

Figure 1:
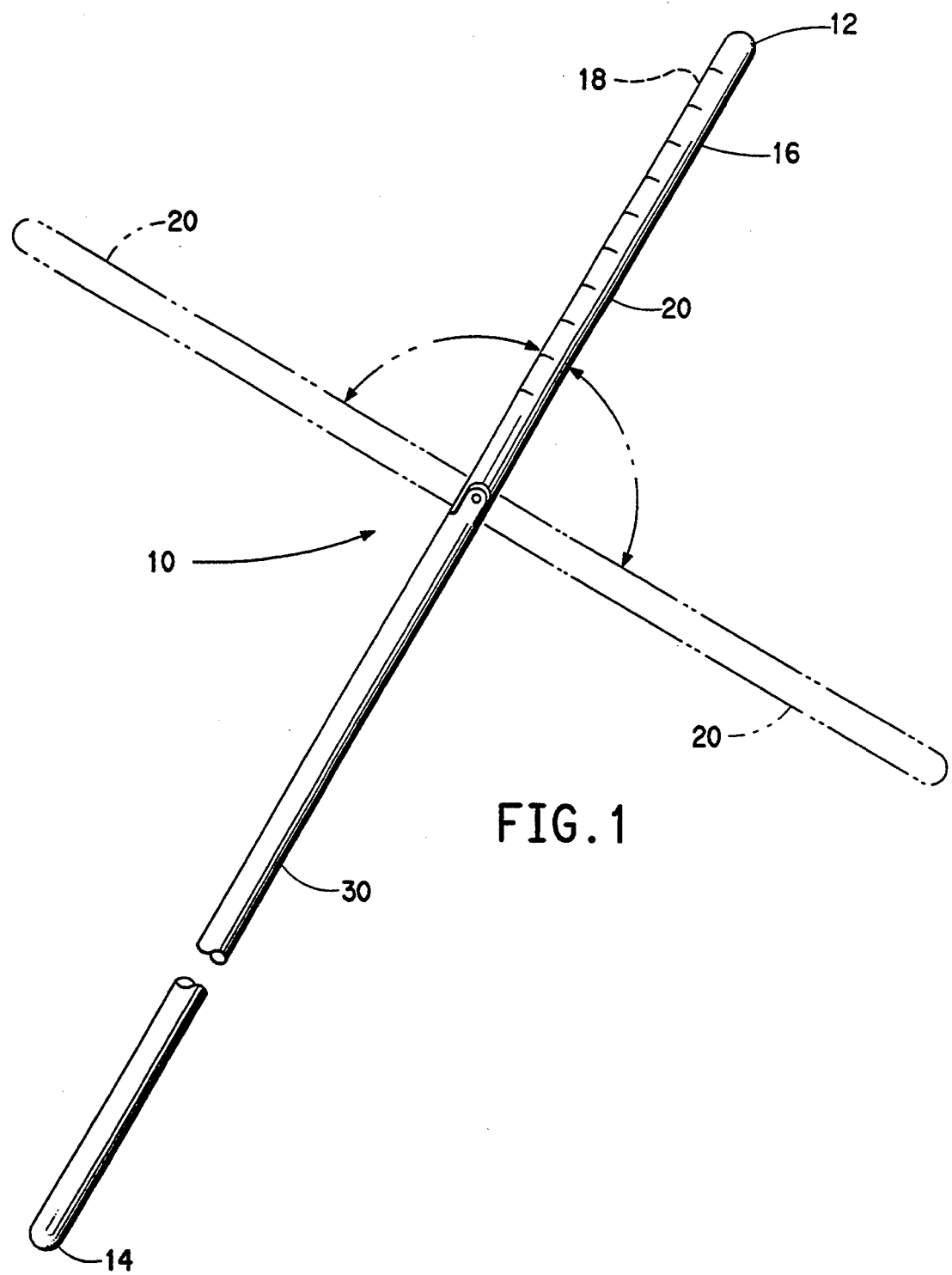
FIG. 1 is a side view of an apparatus in accordance with the present invention shown in phantom in articulated positions.

Referring to FIG. 1, there is a body defect measuring apparatus 10 shown in its articulated position for use in an endoscopic procedure and in accordance with a preferred embodiment of the present invention. While the apparatus 10 is specifically designed for use during an endoscopic hernia repair procedure, it will be appreciated by those skilled in the art that the apparatus can also be used during other endoscopic surgical procedures to measure any body part.

As shown in FIG. 1 and FIG. 2, the apparatus 10 includes a measuring rod 20 and a handle 30. The apparatus 10 is molded and is preferably formed of either a biocompatible plastic or stainless steel. The measuring rod 20 is attached to the distal end 34 of the handle 30 by an attachment hinge 40 which enables the measuring rod 20 to access areas for measurement which are located at an angle relative to the angle at which the apparatus is inserted. While this embodiment is formed of two members which are hingedly attached, the apparatus could also be formed by an integral measuring rod and handle with a flexible portion formed between the two members. The measuring portion 20 includes a measurement indicator 22 which has a plurality of calibrations 24 printed on the anterior 16 and posterior 18 side of the measuring rod 20 for measuring the length and width of the hernia defect.

The calibrations 24 extend from the distal end 26 of measuring rod 20 to the proximal end 28 thereof. Each of the calibrations 24 includes a line 25 and a corresponding number 27. In the preferred embodiment, the calibrations are in centimeters, although any measurement unit could be applied to the measurement rod depending on the size of the body part to be measured. The distal end 26 of the measuring rod 20 is a blunt tip 50 to prevent trauma to the body organs or tissue which might come into contact with the distal end 26 of measuring rod 20.

With reference now to FIGS. 1, 2 and 3, the attachment hinge 40 in the illustrated embodiment is a friction hinge, which in these figures is a cylindrical socket hinge, but could alternatively be a ball socket. The attachment hinge 40 is formed by a receiving member 46 which engages a leg member 44. The receiving member 46 is formed in the distal end 34 of the handle 30 and engages the leg member 44 which extends from the proximal end 28 of measuring rod 20. The leg member 44 includes a pair of oppositely positioned engagement flanges 45 for corresponding engagement with a pair of openings 47 formed in the receiving member 46. The attachment hinge 42 is formed by leg member 44 which is positioned in and received by the receiving member 46. The leg member 44 further includes a pair of oppositely positioned walls 48 which prevent disengagement of the measuring portion 20 from the handle portion 30 by bending. Rotating the handle member permits 360° rotation of the measuring member. As shown in phantom in FIG. 1, with the arrows indicating direction, the attachment hinge further enables up to approximately 180′ rotation of the measuring rod 20 relative to the longitudinal axis of the handle 30.

Figure 4:
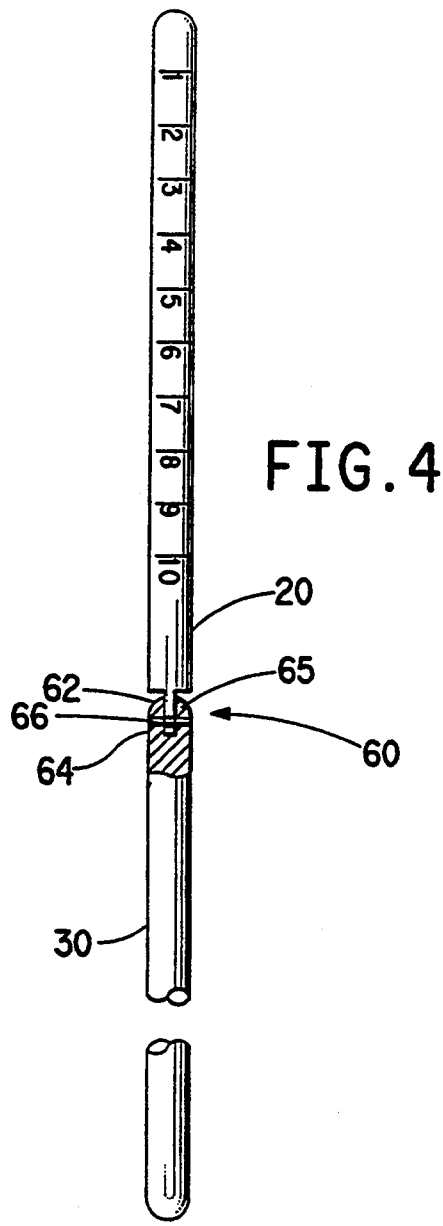
FIG. 4 is a side view of an alternate apparatus in accordance with the present invention.
Figure 5:
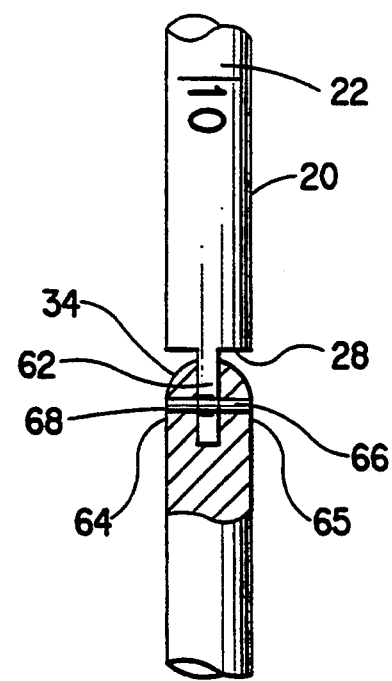
FIG. 5 is an exploded perspective view of the attachment mechanism of the apparatus shown in FIG. 4.

A second embodiment of the subject invention will now be described with reference to FIGS. 4 and 5. This device operates in a matter similar to that of the first embodiment, the sole difference being the structure of the attachment member 60 which in this embodiment is a frictionless hinge attachment. The hinge 60 is formed by a pin 66 which engages a leg member 62. The leg member 62 extends from the proximal end 28 of the measuring rod 20 and includes an opening 68 for receiving the pin 66. The pin 66 extends between oppositely positioned receiving walls 65 formed in the distal end 34 of the handle 30. The pin 66 may be formed of the same material as any element of the apparatus 10, or of another material such as stainless steel.

In yet another embodiment, which is shown in FIG. 8, the apparatus 10 is formed by integral measuring rod 20 and handle 30. A flexible and integral attachment portion 70, which in this embodiment is a living hinge, extends from the distal end 34 of the handle 30 to the proximal end 28 of the measuring rod 20. The attachment portion 70 permits movement of the measuring rod 20 relative to the handle 30 while also providing secure attachment of the handle 30 and the measuring rod 20. The movement and rotation of the measuring rod 20, relative to the handle 30, is determined by the flexibility of the attachment portion 70. The more flexible the attachment portion 70 the more the measuring member 20 will be able to rotate relative to the handle portion 30. The measuring rod 20 includes a plurality of calibrations 24 printed on the flattened anterior side 17 and the flattened posterior side 19.

A further embodiment with an alternative attachment mechanism is shown in FIGS. 10 and 11. A rivet 82 attaches the measuring rod 20 to the handle 30. The rivet 82 extends through countersunk holes, or openings, 84 in the measuring rod 20 and through corresponding countersunk hole 86 in the handle 30.

An additional alternative feature of the invention is shown in FIG. 12 and includes a plurality of radially extending detents 88. The detents 88 are raised from the surfaces of both the handle 30 and measuring rod 20. The detents on both members are arranged in a mating fashion such that the measuring rod is positionable relative to the handle 30.

In use, the apparatus 10 will be inserted into the body cavity through the cannula assembly 52 of a trocar. A laproscopic camera will capture the entry and position of the apparatus in the body cavity, and this image will be reproduced on a monitor which the surgeon will be viewing. While following his or her own movements on the monitor, the surgeon will be able to locate and position the apparatus 10 so that the body part, in this case a hernia defect 56, can be measured. Once the surgeon has positioned the measuring rod so that the body defect can be measured, the surgeon will visually measure the body defect as it is displayed on the monitor. The measuring rod 20 is adapted for 180' positioning with respect to the handle 30, thereby enabling the surgeon to measure hernia defect, which could be located over a wide range of locations relative to the handle 30. Such a feature is advantageous because the majority of hernias are located at an angle approximately 40' relative to a longitudinal axis defined by the length of patient on the surgical table.

Figure 6:
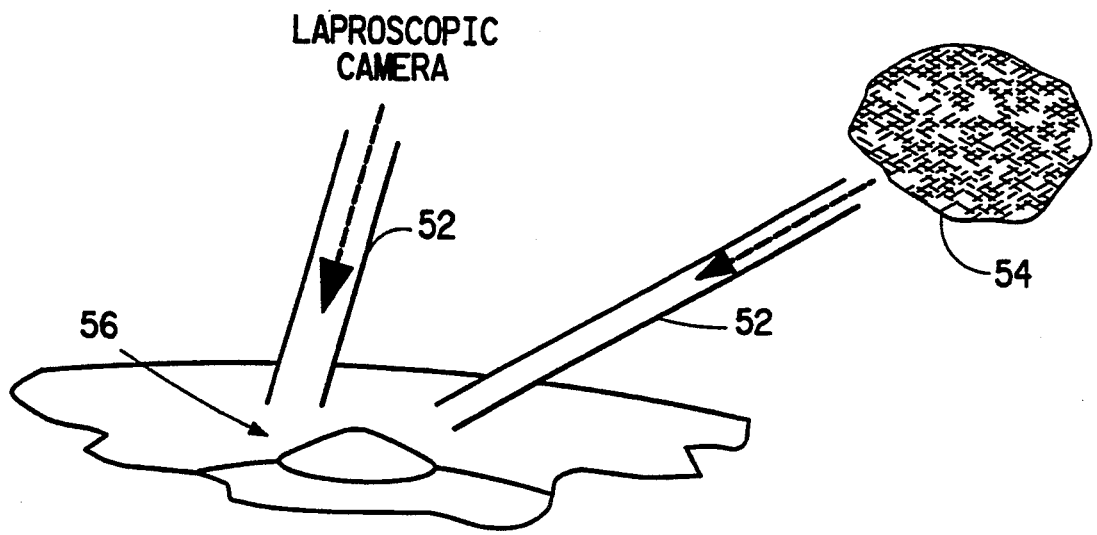
FIG. 6 is a side view of a hernia defect.
Figure 7:
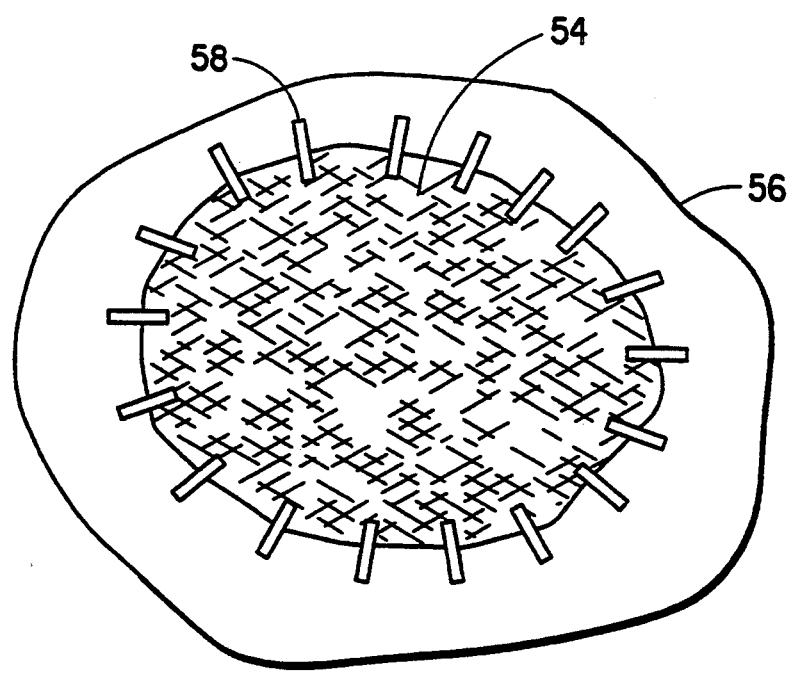
FIG. 7 is a frontal view of a repair in body tissue illustrating one example of an arrangement of staples for attachment of the reinforcing surgical mesh to body tissue in the area of a hernia repair.

During an endoscopic procedure the surgeon manipulates the proximal end 32 of handle 30 to position correspondingly the measuring rod 20. The measurement obtained by the apparatus 10 enables the surgeon to tailor the prosthetic material 54 to the proper size thereby preventing wasted prosthetic material and reducing the operating room time and expense of the procedure. The method of providing a properly sized prosthetic material to the hernia defect is shown in FIG. 6. FIG. 7 shows the placement of staples 58 and their attachment of the prosthetic material 54 to hernia defect 56.

The hernia measuring apparatus can be packaged separately or as part of a kit for endoscopic hernia repair. The kit can include prostheses and a hernia measuring apparatus. An alternative kit can include an apparatus for applying surgical staples during hernia repair, a prosthetic (or mesh) introducer, a hernia measuring apparatus and the prosthesis material.

It will be understood that the foregoing is illustrative of the principles of the invention and that various modifications can be made by those skilled in the art without departing from the scope and spirit of the present invention.

What is claimed is:

1. A method of facilitating endoscopic hernia repair, comprising the steps of:
    inserting a cannula into the body;
    inserting an instrument having a measuring portion into a body cavity through the cannula;
    manipulating said measuring portion to a position adjacent to the body defect so that a plurality of calibrations are adjacent said body defect;
    viewing the size of the body defect on a monitor remote from the body defect by comparing calibrations on the measuring portion to the body defect to determine its size;
    providing prosthetic material based on the determination of the size of the body defect; and
    inserting the prosthetic material through the cannula for positioning over to the hernia.

2. A method as in claim 1, whereas the step of manipulating the measuring portion comprises manipulating a gripping portion of the instrument located remotely from the body defect.

3. A method of facilitating endoscopic hernia repair, comprising the steps of:
    inserting a cannula into the body;
    inserting a measuring instrument into a body cavity through the cannula;
    manipulating a gripping portion of said measuring instrument to pivot a measuring portion pivotally attached to said gripping portion;
    positioning a plurality of calibrations imprinted on said measuring portion adjacent the hernia defect;
    viewing the size of the hernia defect on a monitor remote from the body which shows the images viewed by an endoscope,
    determining the size of the hernia defect by comparing the hernia defect to the calibrations on the measuring portion so that a properly sized prosthetic material can be prepared; and
    positioning prosthetic material over the body defect.

4. A method as in claim 3 further comprising the step of cutting the properly sized prosthetic material and inserting the material and inserting the material through the cannula in order to position it over the body defect.

* * * * *